United States Patent [19]

Teodorescu et al.

[11] 4,070,243
[45] Jan. 24, 1978

[54] METHOD FOR DISTINGUISHING SUBPOPULATIONS IN A POPULATION OF MORPHOLOGICALLY INDISTINGUISHABLE CELLS

[75] Inventors: Marius C. Teodorescu, Oak Park; Eugene P. Mayer; Sheldon Dray, both of Chicago, all of Ill.

[73] Assignee: University of Illinois Foundation, Urbana, Ill.

[21] Appl. No.: 718,807

[22] Filed: Aug. 30, 1976

[51] Int. Cl.$^2$ ............................ C12K 1/02; C12K 9/00
[52] U.S. Cl. .......................................... 195/79; 195/99; 195/101; 195/103.5 R; 195/112
[58] Field of Search ................ 195/103.5 M, 103.5 A, 195/79, 78, 112

[56] References Cited
PUBLICATIONS

Ghetie et al., Eur. J. Immunol. vol. 4 (1974) pp. 500–505.

Primary Examiner—Alvin E. Tanenholtz
Assistant Examiner—C. A. Fan
Attorney, Agent, or Firm—Merriam, Marshall & Bicknell

[57] ABSTRACT

A method for identification of cell subpopulations in a population of cells which are morphologically alike, based on the ability of selected strains of bacteria to bind to the cell surface when they are brought in close contact.

Selected strains of naturally occurring or artificially obtained bacteria of different species or genuses, having an affinity to bind to different subpopulations of a cell mixture, are brought into contact by centrifugation or the like with a mixture of cells such as leukocytes, the mixture is resuspended and the cells having bacteria attached are identified under the microscope. The method is useful particularly for the identification of B cells, several subpopulations of T cells, and the differentiation among leukemic cell populations.

9 Claims, 2 Drawing Figures

METHOD FOR DISTINGUISHING SUBPOPULATIONS IN A POPULATION OF MORPHOLOGICALLY INDISTINGUISHABLE CELLS

BACKGROUND

This invention relates to identification and enumeration of morphologically indistinguishable cells which have different membrane characteristics. More particularly, the invention relates to a method for the identification of subsets of lymphocytes by labeling the cells with selected strains of bacteria which, when brought into close contact with the cells, remain firmly attached and function as labels or markers.

The most widely used methods for identifying subpopulations of cells include the use of specific antibody to detect surface antigens, sedimentation velocity, electrophoresis, and the binding of heterologous erythrocytes. Such methods, however, present a number of disadvantages, such as complexity, cost and inability to distinguish among closely related cell types.

It is known (Ghetie et al., Europ. M. Immunol. 4, 500, 1974) that the bacterial strain of *Staphylococcus aureus*, Cowan I, has the ability to bind to the Fc portion of IgG, thus making it possible to identify cells bearing IgG on their surfaces, although such cells could also be identified by other methods described above. This property of the Cowan I strain of *Staphyloccus aureus* has been looked upon as a not-too-surprising curiosity, since the Fc region of IgG is recognized by other structures such as the Fc receptors on some leukocytes, the first component of complement, and the placental barrier.

SUMMARY OF THE INVENTION

The present invention provides a new, simple and standardizable method for identification of cell subpopulations in a population of cells which are morphologically alike, based on the ability of selected strains of bacteria to bind to the cell surface when they are brought in close contact. The method is useful particularly for the identification of B cells, several subpopulations of T cells, and the differentiation among leukemic cell populations i.e., mixtures of leukocytes.

In accordance with the invention, selected strains of bacteria are used to bind to particular subpopulations of lymphocytes. Naturally occurring or artifically obtained strains of bacteria of different species or genuses, having an affinity for the different subpopulations, are brought into contact by centrifugation or the like with a mixture of lymphocytes, the mixture is resuspended and the cells having bacteria attached are identified under the microscope. By the use of the invention, we have identified five human lymphocyte subpopulations, a result previously unattainable.

DESCRIPTION OF THE DRAWINGS

The invention will be better understood from the following detailed description thereof, taken in conjunction with the accompanying drawings, in which.

DETAILED DESCRIPTION

Selection of Bacteria

Figure 1:
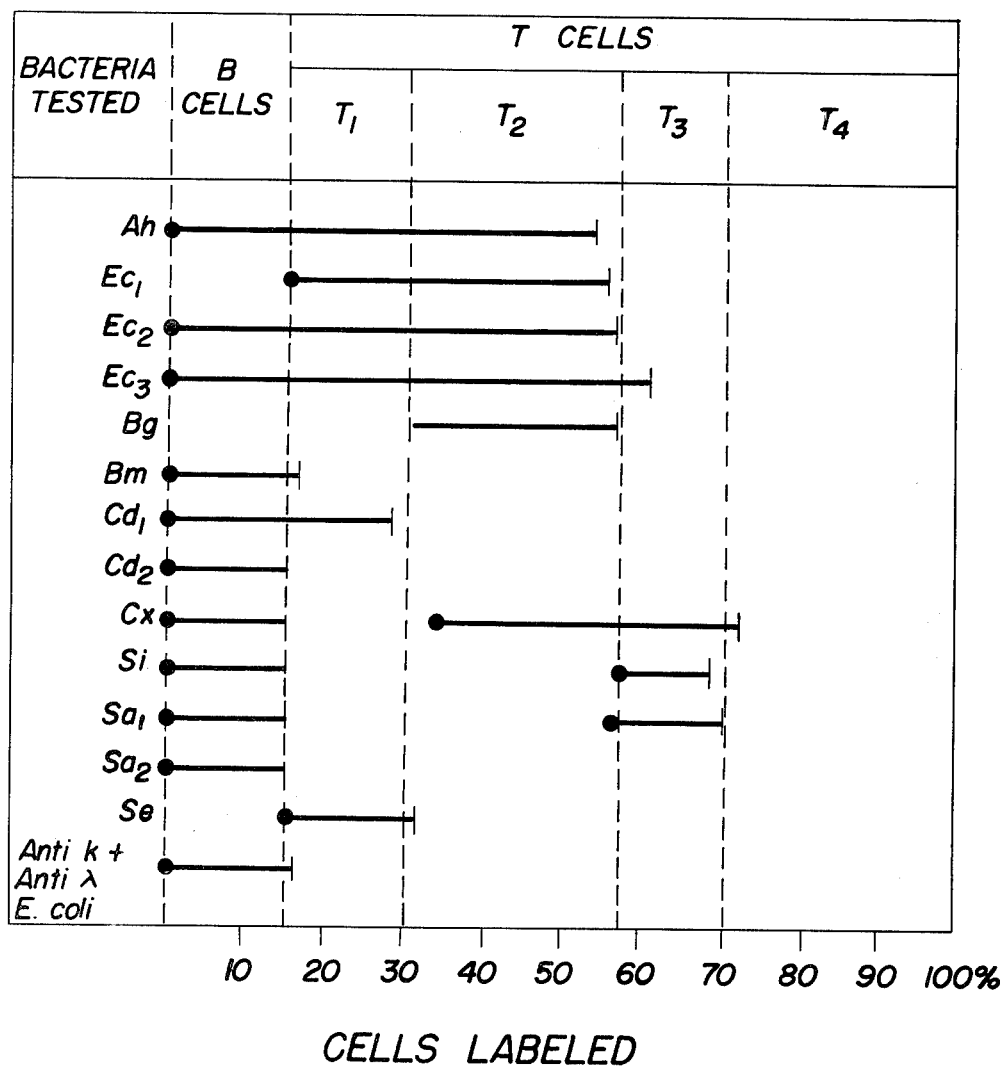
FIG. 1 is a graph showing the differential binding to normal lymphocytes of strains of bacteria useful in the invention.

Bacteria to be screened for use in the invention are grown, fixed with formaldehyde, washed and maintained as suspensions. The bacteria must be small enough to permit a sufficient number of bacteria to bind to the animal cell to permit identification, but still visible under the light microscope. Bacteria having longest dimensions between 0.2-2.0 microns are particularly useful.

To test whether a bacterial strain naturally or artificially prepared or selected is useful for the study of an animal cell surface, the bacterial cell suspension is centrifuged together with the animal cells at a ratio of 100-200 bacteria for each animal cell. The cells are resuspended by vigorous pipetting and examined under phase contrast microscopy. Alternatively, bacterial cells can be washed out, the cells smeared, stained and examined under a regular bright field microscope.

In such manner, the strains of bacteria given in Table I have been found to bind to human lymphocyte population to a significant degree (greater than about 10% of the cells). The unexpected and unpredictable nature of bacterial binding to cells is demonstrated by the fact that, out of 4 strains of *E. coli* tested, one did not bind to any lymphocyte, two bound to B cells, $T_1$ cells, and $T_2$ cells and one bound only to $T_1$ cells.

In addition to selection among naturally occurring strains of bacteria, the invention also contemplates a method for screening artificial mutants suitable for use therein. A strain of bacteria which requires a particular nutrient for its growth, e.g., a strain of *E. coli* which is tryptophan dependent (delection mutant), is treated with a mutagenic agent, e.g., ultraviolet light. The treated bacteria are grown in large numbers (e.g., over $10^{11}$ cells) and are brought into close contact with the animal cells for which a marker is sought. Excess bacteria (i.e., those that did not bind to an animal cell) are washed. The animal cells are plated onto a suitable medium, such as a soft agar plate or the like, which lacks the required nutrient, i.e., tryptophan, in the assumed example. The bacteria which were bound to animal cells will obtain the required nutrient from the cells and will grow into a colony. The bacteria in the colonies are grown and investigated for binding properties as described above.

TABLE I

| | BACTERIA WHICH BIND TO CELLS | |
|---|---|---|
| STRAIN | DESIGNATION NO. | SPECIES |
| Ah | *ATCC 31241 | *Arizona hinshawii* |
| $Ec_1$ | **NRRL-B-11009 | *Escherichia coli* |
| $Ec_2$ | NRRL-B-11010 | " |
| $Ec_3$ | NRRL-B-11011 | " |
| Bg | NRRL-B-11007 | *Bacillus globigii* |
| Bm | ATCC 31242 | *Brucella militensis* |
| $Cd_1$ | ***UI 43 | *Corynebacterium diptheriae* |
| $Cd_2$ | UI 44 | " |
| Cx | NRRL-B-11008 | *Corynebacterium xerosis* |
| Sl | NRRL-B-11012 | *Sarcina luetea* |
| $Sa_1$ | ATCC 31240 | *Staphylococcus aureus* |
| $Sa_2$ | UI 57 | " |
| Se | NRRL-B-11013 | *Staphylococcus epidermidis* |

*Bacteria designated by "ATCC" have been deposited in the American Type Culture Collection, 12301 Parklawn Drive, Rockville, Maryland 20852.

**Bacteria designated by "NRRL" have been deposited in the ARS Culture Collection, Northern Regional Research Center, U.S. Department of Agriculture, Peoria, Illinois, 61604.

***Bacteria designated by "UI" have been deposited in a collection maintained by the Dept. of Microbiology, College of Medicine, University of Illinois at the Medical Center, Chicago, Illinois 60612.

All of the bacteria identified in Table I will be made permanently available to the public in accordance with the Commissioner's Notice of Apr. 29, 1971 (886 O.G. 638).

Identification of Cell Populations

To analyze whether bacteria found to bind to lymphocytes bind to similar or different subpopulations, the following procedure is used. The lymphocyte suspension is prelabeled with one bacteria and the excess of bacteria is washed out by centrifugation at low speed, which allows the sedimentation only of animal cells but not of bacteria. To the prelabeled suspension is added a different bacteria, and the mixture is centrifuged and examined. Three sets of figures (percentages) are obtained: (1) cells labeled with the first bacteria, (2) cells labeled with the second bacteria, and (3) cells labeled with both bacteria. By using various combinations of bacteria a mapping of the cell population is possible. To compare the subpopulations observed by this method with those already known through other methods, e.g., by the use of antibody, the bacterial strain under study is tested on suspensions prelabeled with bacteria chemically coated with antibody directed against a particular cell subpopulation. For example, a bacterial strain which does not bind spontaneously to lymphocytes is coated with anti-immunoglobulin antibody, making it bind to B cells. Based on these procedures, certain bacterial strains (See Table II) have been found which bind to B cells, thus replacing the need for the use of antibody coated bacteria which are much more difficult to prepare. When the examination of lymphocytes is carried out in stained smears, the observation of the other leukocytes, i.e., monocytes, neutrophils, basophils, and eosinophils, is possible, as well as the study of their subpopulations. After the binding properties of one particular bacterial strain of a particular cell subset is established in normal individuals it becomes a biological constant which can be used for diagnosis of disease.

Patterns of Binding by a Panel of Bacterial Strains

In many instances it is difficult or impossible, using known procedures, to distinguish between two cell populations which are morphologically and numerically alike. For example, chronic lymphocytic leukemia with B cells have different clinical evolution, although the cell populations look alike in vitro. Leukemias with leukocytes which are difficult to identify are often called "unclassifiable".

To identify cell populations which are so similar, for which the antibody method could not be applied, the use of a panel of bacteria, especially selected, offers a method for distinguishing patterns of binding which are chracteristic to a certain population. Bacteria are selected for such pattern studies based on the variability of binding. For example, if one particular bacteria binds 5%, 25% and 75% of the cells of three different populations, it is useful to differentiate among such populations.

The use of bacterial strains in accordance with the invention to measure the extent of diversity of particular cell populations in different individuals, particularly those having blood cell diseases, is illustrated in the following examples.

EXAMPLE 1

Use of Bacterial Strains to Detect and Identify Subpopulations of Human Lymphocytes

Purification of Peripheral Blood Lymphocytes

Peripheral blood lymphocytes were obtained by a two-step purification procedure devices to remove most of the monocytes, thrombocytes and granulocytes. The blood (10 ml) was collected on heparin, applied to a glass wool column and incubated at 37° C for 45 minutes. The blood cells were eluted with prewarmed Eagle's Minimal Essential Medium (MEM) (Gibco, Grand Island, N.Y.) and the lymphocytes were purified on Ficoll-Hypaque. To determine the efficiency of the two-step purification, the cells, in some cases, were purified only on Ficoll-Hypaque. To estimate the purity of the lymphocyte suspensions, the cells were smeared by use of cytocentrifuge and stained with Wright stain to obtain a differential count.

Preparation of Bacterial Cell Suspensions

Bacteria were obtained from the collection of the Department of Microbiology, College of Medicine, University of Illinois, at the Medical Center, Chicago, Ill., and had been isolated from patients in the hospital laboratory. The bacteria used are those given in Table I.

A strain of *E. coli* which did not bind to lymphocytes was coated with purified anti-$\kappa$ and anti-$\lambda$ light chain antibodies and is referred to as *E. coli*. *Streptococcus lactis* which also did not bind to lymphocytes was used in control experiments. The bacteria were grown as suspensions in Difco antibiotic medium III (Difco, Detroit, Michigan) under continuous aeration, were harvested in the late log phase, and were washed with saline. They were used either as unfixed preparations containing sodium azide (0.04%) or as fixed preparations obtained by treating the bacteria overnight with 10% formaldehyde in phosphate buffered saline and washing them with saline. The final suspensions contained about $10^9$ bacteria/ml.

Assay for Binding of Bacteria to Lymphocytes

Lymphocyte suspensions in MEM containing 1% bovine serum albumin (BSA) and 0.02% sodium azide were mixed with bacteria at a ratio of 200 bacteria for each lymphocyte and centrifuged at 900 × g for 3 minutes. The pellet was resuspended by vigorous pipetting and examined by phase contrast microscopy; the cells with attached bacteria could be readily distinguished. The granuloctytes still present in the lymphocyte suspensions were easily distinguishable and could be eliminated from the count. The same method was used to count B cells by using anti-Ig (anti-$\kappa$ and anti-$\lambda$) antibody coated *E. coli*.

Labeling B Cells (Ig+) with Antibody Coated Bacteria in Stained Blood Smears The unseparated blood cells (0.2 ml) were washed three times with 2.5 ml of MEM supplemented with 6% Bovine Serum Albumin and the B cells were labeled with *E. coli* coated with purified anti-light chain antibody as previously described, Teodorescu et al., *Cell Immunol.* 24, 90, 1976. Briefly, 0.1 ml of washed blood cells (erythrocytes and leukocytes included) were mixed with *E. coli* which had been coated by glutaraldehyde with purified anti-$\kappa$ and anti-$\lambda$ human light chain antibodies. The washed blood cells were mixed with the antibody-coated bacteria at a ratio of 10 bacteria for each cell (white and red included). The mixture was centrifuged at 900 × g for 6 minutes, resuspended in 6% BSA in MEM and centrifuged at 150 × g for 10 minutes to remove unbound bacteria. The pelleted cells were smeared and stained with Wright stain.

and unfixed bacteria, fixed bacteria were used in the experiments presented here. Each strain of bacteria bound a percentage of the lymphocyte population ranging from 14% for $Sa_2$ to 61% for $Ec_3$ (See Table II).

Percentages of Lymphocytes Binding Bacteria Before and After Prelabeling Either With Anti-Ig Antibody-Coated *E. Coli* or With a Different Bacteria

| Bacteria | Nothing[a] % | Anti-Ig Ab *E. coli* % | $Ec_2$ % | Bg % | Cx % | Se % | $Sa_1$ % | Sl % | $Cd_1$ % |
|---|---|---|---|---|---|---|---|---|---|
| Ah | 54±2.5[c] | 57 ± 1.2 | 58 ± 1.9 | ND | ND | ND | ND | ND | ND |
| $Ec_1$ | 41±2.6 | 56 ± 3.5 | 59 ± 3.5 | 45 ± 1.9 | 67 ± 2.9 | 45 ± 1.8 | 69 ± 1.5 | ND | 55±4.9 |
| $Ec_2$ | 56±0.9 | 57 ± 1.5 | ND | ND | 71 ± 3.2 | ND | ND | ND | ND |
| $Ec_3$ | 61±1.2 | 62 ± 1.2 | 60 ± 1.2 | ND | ND | ND | ND | ND | ND |
| Bg | 26±1.5 | 43 ± 3.2 | 58 ± 3.2 | ND | ND | ND | ND | 46±2.6 | ND |
| Bm | 16±0.8 | 16 ± 1.2 | 57 ± 1.5 | 42 ± 3.5 | ND | ND | ND | ND | ND |
| $Cd_1$ | 28±0.5 | 27 ± 0.8 | 57 ± 1.5 | 52 ± 1.5 | ND | 31 ± 2.4 | 41 ± 1.2 | ND | ND |
| $Cd_2$ | 15 ± 1.5 | 16 ± 0.8 | 63 ± 3.5 | ND | ND | ND | ND | ND | ND |
| Cx | 50±3.8 | 50 ± 1.2 | 72 ± 3.2 | 53 ± 1.5 | ND | 72 ± 2.2 | 52 ± 3.9 | ND | 69±2.5 |
| Sl | 26 ± 1.9 | 24 ± 1.9 | 67 ± 3.5 | 48 ± 2.3 | 52 ± 1.5 | ND | 33 ± 2.9 | ND | 43±2.1 |
| $Sa_1$ | 30 ± 2.3 | 32 ± 2.4 | 71 ± 1.7 | 54 ± 2.4 | ND | 44 ± 1.8 | ND | 31 ± 2.3 | ND |
| $Sa_2$ | 14 ± 0.8 | 17 ± 1.2 | 57 ± 1 | ND | ND | ND | ND | ND | ND |
| Se | 16 ± 1.2 | 30 ± 1.7 | 56 ± 4.9 | 40 ± 2.5 | 68 ± 3.2 | ND | ND | 43 ± 1.8 | 28±1.5 |
| *S. lactis* | 0 | 16 ± 1.5 | 57 ± 1.9 | ND | ND | ND | ND | ND | ND |
| Anti-Ig Ab *E. coli*[b] | 17 ± 1.2 | ND | ND | ND | ND | ND | ND | ND | ND |

[a]Purified lymphocyte suspension not pretreated with other bacteria
[b]*E. coli* which did not bind spontaneously to any lymphocyte was coated by glutaraldehyde with anti-κ and anti-λ light chain antibodies (anti-IgAb)
[c]mean value ± standard error of the mean.
ND = Not done

The Lymphocyte Population

The lymphocytes used in this study were cells which did not adhere to glass and which did not pellet during Ficoll-Hypaque purification. Smears of lymphocyte purified only on Ficoll-Hypaque contained 15–18% monocytes while the lymphocyte suspensions obtained after purification on glass wool and Ficoll-Hypaque contained 2% monocytes. The removal of monocytes was required since they tend to bond some of the bacteria tested as well as to the anti-κ and anti-λ antibody coated bacteria and they are difficult to distinguish from lymphocytes by phase contrast microscopy. At the same time, the glass wool purification step eliminated the thrombocytes which would bind to the cells and complicate the phase contrast examination of cells binding bacteria. The small percentage of granulocytes (about 10%) remaining in the lymphocyte suspensions did not interfere with the phase contrast reading since they were readily distinguishable.

In the cell population obtained by the two-step purification procedure, the percentage of Ig+ cells was 17%, whereas the percentage of Ig+ cells was 29–32% in cell populations obtained by purification only on Ficoll-Hypaque, since most monocytes appear as Ig+ cells. The 17% Ig+ cells found in the population of lymphocytes purified by glass wool and Ficoll-Hypaque was similar to the 18% Ig+ lymphocytes determined in stained smears of the unseparated blood cell population (in the stained smears, monocytes were eliminated from the count by morphological criteria).

Binding of Bacteria to Normal Human Lymphocytes

The lymphocytes of normal donors were used to test the binding properties of 53 different strains of bacteria. The bacteria listed in Table I were found to bind to a significant percentage of lymphocytes (>10%) and were used in subsequent experiments. Unfixed bacteria were used in the initial screening. Since no significant differences were noticed between the binding of fixed and unfixed bacteria, fixed bacteria were used in the experiments presented here. Each strain of bacteria bound a percentage of the lymphocyte population ranging from 14% for $Sa_2$ to 61% for $Ec_3$ (See Table II).

To establish whether the bacteria bound to B or T cells or to different subpopulations of them, the percentages of lymphocytes that bound each strain of bacteria were determined on three preparations of lymphocyte suspensions: (a) untreated purified lymphocytes, (b) lymphocytes pretreated with anti-Ig antibody-coated *E. coli,* and (c) lymphocytes pretreated with another strain of bacteria. The pretreatment was carried out as follows: the lymphocytes were mixed with the bacteria at a ratio of 1:200; the mixture was centrifuged at 900 × g for 6 minutes; to remove the unbound bacteria, the pellet was resuspended in MEM containing 6% BSA; the cells were centrifuged at 150 × g for 10 minutes; the supernatant containing most of the bacteria was discarded.

The percentage of lymphocytes labeled with each strain of bacteria was compared to the percentage of lymphocytes labeled when the same strain was tested on cells prelabeled with anti-Ig antibody-coated *E. coli* (compare columns 2 and 3 of Table II). The following observations and conclusions were made; (1) no significant increase in the percentage of labeled lymphocytes occurred for Ah, $Ec_2$, $Ec_3$, Bm, $Cd_1$, $Cd_2$, Cx, Sl, $Sa_1$, and $Sa_2$ when the lymphocytes were pretreated with antibody-coated *E. coli;* thus, these bacteria labeled at least all of the Ig+ cells; (2) all of the percentages of labeled cells obtained using Ah, $Ec_2$, $Ec_3$, $Cd_1$, Cx, Sl and $Sa_1$ were higher than the percentages of Ig+ cells; thus, these bacteria identified all of the Ig+ cells and a part of Ig− cells; (3) no significant increase in the percentage of labeled cells was observed when the lymphocytes were prelabeled with anti-Ig antibody-coated *E. coli* and tested with Bm, $Cd_2$, or $Sa_2$; the percentage of Ig+ cells was similar to the percentages of lymphocytes labeled with any of these three strains of bacteria (16%, 15%, and 14%, respectively); thus, Bm, $Cd_2$, and $Sa_2$ identified only Ig+ cells; (4) other bacteria, $Ec_1$, Bg, and Se, yielded higher percentages when the lymphocytes were prelabeled with anti-Ig antibody-coated *E. coli,* the difference being approximately equal to the percentage of Ig+ cells; thus, they only labeled a fraction of the Ig− cell population.

The results obtained by labeling with various combinations of bacteria were analyzed and the "puzzle" in FIG. 1 was arranged as the pattern for the binding of bacterial strains to lymphocyte subpopulations. The identification of the Ig− cell subpopulations was based on the following reasoning. (1) When each bacteria was tested on lymphocytes prelabeled with $Ec_2$, the highest value obtained was 72% and $Ec_2$ labeled 56% of the cells which included all Ig+ lymphocytes; thus, a subset of Ig− cells (T4, FIG. 1) was not recognized by any of the bacteria tested. (2) Cx recognized 50% of the lymphocytes including the Ig+ cells and, at the same time, there was an increase from 56% recognized only by $Ec_2$ to 72%, recognized by $Ec_2$ together with Cx; thus, Cx recognized a subset of Ig− cells not labeled by $Ec_2$ ($T_3$, FIG. 1). (3) The remaining two subpopulations of T cells were identified as follows: Se identified approximately 15% of the lymphocyte population and did not, as stated above, identify and Ig+ cells; $Ec_2$ recognized 56% of the population of which about 15% were Ig+ cells (see above); thus about 40% of the cells recognized by $Ec_2$ were Ig− cells. When Se was added to lymphocytes prelabeled with $Ec_2$ there was no increase in the percentage of labeled cells compared to the percentage obtained only with $Ec_2$; thus, the fraction of Ig− cells that was recognized by Se was also recognized by $Ec_2$. Since $Ec_2$ identified significantly more Ig− cells than did Se, two more subpopulations of Ig− cells were present which were identified by $Ec_2$ ($T_1$ and $T_2$, FIG. 1), of which $T_1$ but not $T_2$ was identified by Se. The other bacteria were placed in the "puzzle" based on similar reasoning.

We conclude that Ig+ cells (B cells) appeared as one population which was identified by all of the bacteria tested except $Ec_1$, Se, and Bg. Also, Bm, $Cd_2$, and $Sa_2$ bound exclusively to B cells. We also conclude that Ig− cells (T cells) could be subdivided into four subpopulations (FIG. 1). $T_1$ cells, about 15% of the lymphocytes, were labeled by Ah, $Ec_1$, $Ec_2$, $Ec_3$, $Cd_1$ and Se; the last (Se) identified only $T_1$ cells. $T_2$ cells, approximately 25% of the lymphocytes, were labeled by Ah, $Ec_1$, $Ec_2$, $Ec_3$, Cx and Bg; the last (Bg) recognized exclusively $T_2$ cells. $T_3$ cells, about 15% of the lymphocytes were labeled by Cx, Sl, and $Sa_1$. $T_4$ cells, about 30% of the lymphocytes, were not recognized by any of the bacteria tested. B cells and three subsets of T cells were found to bind bacteria with the following distribution in terms of number of subsets bound by each strain. Some bacteria bound three subsets: Ah, $Ec_2$ and $Ec_3$ bound to B, $T_1$ and $T_2$; Cx bound to B, $T_2$ and $T_3$. Some bacteria bound to two subsets: $Ec_1$ to $T_1$ and $T_2$; Sl or $Sa_1$ to B and $T_3$. Other bacteria bound only one subset: Bm, $Cd_2$, and $Sa_2$ to B cells; Se to $T_1$ cells; Bg to $T_2$ cells (FIG. 1).

The lymphocytes of the same individual were tested four times within 10 days for their ability to bind bacteria. The percentages of lymphocytes binding $Ec_2$, Cx, $Cd_1$, Bm or antibody-coated E. coli did not change significantly within this time interval. The binding of other bacteria showed similar reproducibility.

Five normal individuals were tested for the ability of their lymphocytes to bind some of the bacteria used (Table III). The percentages were fairly similar for each of the bacteria tested. The variation in the percentage of Ig+ cells, i.e., 11% to 24%, correlated with the percentages of lymphocytes labeled with Bm and $Cd_1$ providing further evidence that these two bacteria are B cell markers.

TABLE III

Binding of Bacteria by Lymphocytes from Normal Individuals

| Bacterial Strain | Percentage of Lymphocytes binding bacteria for five donors | | | | |
|---|---|---|---|---|---|
| | Mte[a] | Ate | Gma | Rkl | Nko |
| | %±S.e[b] | %±S.e | %±S.e | %±S.e | %±S.e |
| $Ec_1$ | 41±2.6 | 40±2.0 | 44±3.0 | 30±3.5 | 31±4.0 |
| $Ec_2$ | 56±0.9 | 61±1.5 | 58±3.0 | 63±3.5 | ND |
| Bg | 26±1.2 | 31±2.0 | 29±0.0 | ND | ND |
| Bm | 16±0.8 | 21±2.0 | 20±2.5 | 11±1.7 | 22±2.0 |
| $Cd_1$ | 28±0.5 | 36±2.5 | 31±3.0 | 10±2.5 | 31±2.0 |
| $Cd_2$ | 15±1.5 | 20±2.0 | 20±1.0 | 24±0.5 | 19±1.5 |
| Cx | 50±3.8 | ND[c] | 60±5.0 | 54±4.5 | ND |
| Sl | 26±1.9 | 35±1.0 | 30±1.0 | 25±3.0 | 42±2.5 |
| $Sa_1$ | 14±2.3 | 24±2.0 | 21±1.5 | 12±1.5 | 18±1.5 |
| $Sa_2$ | 16±0.8 | 15±1.5 | 16±1.5 | 11±1.5 | ND |
| E. coli | 0 | 0 | 1 | 0 | ND |
| anti-Ig E. coli | 17±1.2 | 24±1.2 | 20±0.5 | 11±2.1 | 23±3.0 |

Figure 2:
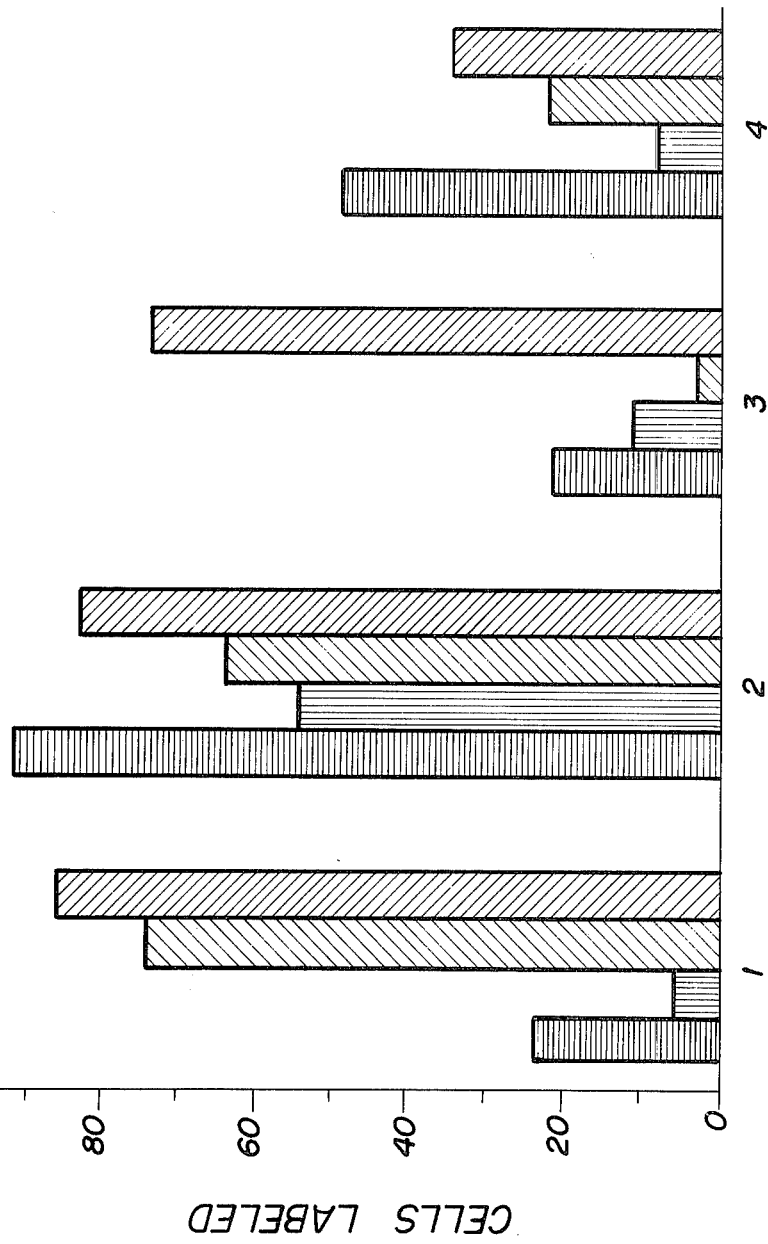
FIG. 2 is a graph showing the pattern of binding by several bacteria to the lymphocytes of leukemic patients.

[a]The lymphocytes from Donor Mte were used for the experiments presented in Table II and FIG. 2.
[b]s.e = standard error of the mean.
[c]ND = not done The pattern of labeling the lymphocyte population with various strains of bacteria can be explained by the existence of one population of B cells and four subpopulations of T cells. One subpopulation of T cells did not bind any of the bacteria tested.

Lymphocyte subpopulations have been shown to have unique markers as well as markers shared in common by at least two subsets of lymphocytes.

The Cowan I strain of S. aureus is known to bind to the Fc region of IgG and thus to identify only a relatively small fraction of the B cell population bearing this class of Ig on the surface. The three bacterial strains in our experiments, Bm, $Cd_1$ and $Sa_2$, bound to all B cells indicating that the binding mechanism is different from that described for the Cowan I strain.

Another unexpected observation resulting from this study was that taxonomically different bacteria, e.g., Ah and $Ec_2$ or Sl and $Sa_1$, bound to the same subsets of lymphocytes. On the other hand, we observed that different strains of the same species have variable binding properties, e.g., $Ec_1$ did not bind to B cells; $Ec_2$ and $Ec_3$ bound to B, $T_1$ and $T_2$ cells; the E. coli strain used for antibody-coating did not bind to any lymphocytes. The selective binding of bacteria to lymphocytes is thus useful for the study of bacterial strains and their pathogenicity.

The method of the invention is useful for the study of the differentiation, the functional and structural diversity, and the abnormalities of lymphocyte populations. For example, the binding of some bacterial strains was used to distinguish at least four patterns of bacterial binding in leukemic cell populations.

EXAMPLE 2

The Pattern of Binding of Bacteria to Leukemic Cell Populations

The same methodology and bacteria were used to label leukemic cell populations in order to distinguish them from normal lymphocyte populations or to distinguish among leukemic cell populations. (See Table IV).

TABLE IV

PERCENTAGES OF LYMPHOCYTES BINDING DIFFERENT BACTERIA IN LEUKEMIC PATIENTS

| Bacteria Tested | CLL-1 % | CLL-2 % | CLL-3 % | CLL-4 % | CLL-5 % | CLL-6 % | CLL-7 % | cll-8 % | NORMAL CONTROLS (5) Mean | Range |
|---|---|---|---|---|---|---|---|---|---|---|
| $Ec_1$ | 88±0.7 | 95±1.7 | 95±1.8 | 87±3.2 | 89±1.8 | 90±2.6 | 78±1.0 | ND | 37 | 30–44 |
| $Ec_2$ | 23±1.8 | 92±0.9 | 21±3.2 | 49±2.3 | 41±3.0 | 71±3.0 | 49±3.5 | 87±2.5 | 59 | 56–63 |
| Bg | 6±0.9 | 53±3.8 | 11±3.0 | 8±1.8 | 14±1.5 | ND | 10±2.0 | 44±3.0 | 29 | 26–31 |
| Bm | 91±1.7 | 93±1.2 | 88±3.2 | 83±1.5 | 85±2.0 | 82±1.5 | 80±1.5 | 91±5.0 | 18 | 11–22 |
| $Cd_1$ | 51±1.5 | 86±1.8 | 65±1.2 | 49±2.0 | 53±1.5 | 41±3.5 | 46±2.5 | 58±2.5 | 27 | 10–36 |
| $Cd_2$ | 10±1.5 | 21±1.8 | 7±1.9 | 28±3.0 | ND | 12±1.0 | 5±0.5 | ND | 20 | 15–24 |
| Cx | 85±1.8 | 97±0.9 | 87±3.4 | 87±3.5 | ND | 81±2.0 | 61±1.5 | ND | 61 | 50–80 |
| Sl | 75±3.0 | 63±3.6 | 3±1.2 | 22±1.0 | 22±2.5 | ND | 21±2.5 | 61±4.5 | 32 | 25–42 |
| $Sa_1$ | 86±0.9 | 83±1.5 | 74±2.0 | 35±2.0 | 31±3.0 | 46±3.0 | 30±2.0 | 78±1.5 | 18 | 12–24 |
| Se | 12±1.2 | 27±1.2 | 21±5.0 | 15±2.5 | ND | 29±3.0 | 10±1.5 | ND | 15 | 11–16 |
| E. coli | 0 | 1 | 1 | 2 | 0 | 1 | 1 | ND | — | 0 – 1 |
| E. coli coated with anti-κ + anti-λ antibody | 70±2.1 | 61±1.2 | 52±4.5 | 53±1.0 | 66±2.5 | 62±3.0 | 68±2.0 | 77±2.5 | 19 | 11–24 |

ND = not done

The number of Ig+ cells determined by labeling with E. coli coated with anti-light chain antibodies was much higher in CLL patients than in normals, i.e., 52–77% in CLL compared to 11–24% in normal individuals (Table IV). E. coli coated with normal rabbit IgG did not bind to leukemic or to normal lymphocytes. The high percentage of Ig bearing cells is a characteristic of chronic lymphocytic leukemias.

The percentages of leukemic lymphocytes which bound $Ec_1$ and Bm were always higher than the normal range, i.e., for $Ec_1$, 78–95; % compared to 30–44% and for Bm, 83–93% compared to 11–22%. Thus, in addition to anti-Ig Ab coated E. coli, $Ec_1$ and Bm can also be used to identify leukemic lymphocyte populations. The increase in the labeling of leukemic compared to normal lymphocyte populations was higher for Bm than for $Ec_1$ or anti-Ig antibody-coated E. coli. Thus, labeling with Bm appears to be the most useful for distinguishing between CLL and normal lymphocyte populations (Table IV), i.e., the ranges obtained for leukemic and normal cell populations are further apart for Bm than for $Ec_1$ or antibody-coated E. coli.

Differences between normal and leukemic cell populations were also recorded when the labeling was carried out with the other bacteria ($Ec_2$, Bg, $Cd_1$, $Cd_2$, Cx, Sl, Sa, and Se) which had been used to characterize normal lymphocyte populations. However, the differences were not consistent in all the patients, the CLL lymphocyte populations having higher, lower or almost normal percentages of cells labeled with bacteria (Table IV). However, some differences between CLL-populations in binding bacteria were considered.

In order to observe differences between leukemic cell population from different patients with leukemia, a panel of 4 bacteria were used which manifested the larges variability in binding lymphocytes from different patients, i.e., $Ec_2$, Bg, Sl and $Sa_1$. The percentages of lymphocytes binding these strains of bacteria were plotted on a graph (FIG. 2) for the first four patients in Table IV. Four different patterns were observed. The first pattern is characterized by relatively low levels for $Ec_2$ and Bg and relatively high percentages for Sl and $Sa_1$. Pattern two had relatively high levels for all four strains. Pattern three had relatively low levels for $Ec_2$, Bg and Sl and high for $Sa_1$. The fourth pattern had relatively low levels for all four bacteria. The remaining four patients fell into these four patterns: CLL-5, CLL-6 and CLL-7 into pattern four and CLL-8 into pattern two.

All patients used had high numbers of total leukocytes (over 50,000), with percentages of lymphocytes exceeding 80%. for an increase in the total largest of lymphocytes from about $2 \times 10^6$/ml to over $40 \times 10^6$/ml, it was expected that over 90% of the lymphocyte population consisted of leukemic lymphocytes. Although the method used to identify Ig+ cells, i.e., the labeling with antibody-coated bacteria appeared to be very sensitive, the percentages of Ig+ cells in B cell leukemias described here ranged from 52% to 77%. The percentages of lymphocytes labeled with Bm and $Ec_1$ ranged from 78% to 95%, closer to the expected percentage of leukemic cells of about 90%. The property of binding these two strains of bacteria therefore has diagnostic value in the counting of the actual number of "abnormal" lymphocytes.

The method of the invention was used to distinguish between normal and leukemic lymphocyte populations and to distinguish at least four patterns of bacterial binding with leukemic cells. Some bacteria appeared to be useful to differentiate normal from leukemic lymphocyte populations, others to distinguish among leukemic cell populations.

The foregoing detailed description has been given for clearness of understanding only, and no unnecessary limitations should be understood therefrom, as modifications will be obvious to those skilled in the art.

What is claimed is:

1. A method for detecting, identifying and enumerating a subpopulation of leukocytes in a mixture of morphologically indistinguishable leukocytes having different membrane characteristics, which method comprises bringing said mixture into close contact with a previously selected strain of bacteria having an affinity for binding only to the cells of said subpopulation by a mechanism not involving the binding sites of any immunoglobulins on the surface of said leukocytes, and observing the presence of said bacteria bound to said subpopulation as a morphologically distinct marker for identification and enumeration of said subpopulation.

2. The method of claim 1 wherein unbound bacteria are removed and said mixture is inspected as a stained smear for the presence of bound bacteria.

3. The method of claim 1 wherein unbound bacteria are not removed and said mixture is inspected by phase contrast microscopy for the presence of bound bacteria.

4. The method of claim 1 wherein said cells are lymphocytes and said bacteria is selected from the group consisting of *Arizona hinshawii*, ATCC 31241; *Escher-* ichia coli, NRRL-B-11009; *Escherichia coli*, NRRL-B-11010; *Escherichia coli*, NRRL-B-11011; *Bacillus globigii*, NRRL-B-11007; *Brucella militensis*, ATCC 31242; *Corynebacterium diptheriae*, UI 43, *Corynebacterium diptheriae*, UI 44; *Corynebacterium xerosis*, NRRL-B-11008; *Sarcina luetea*, NRRL-B-11012; *Staphylococcus aureus*, ATCC 31240; *Staphylococcus aureus*, UI 57; *Staphylococcus epidermidis*, NRRL-B-11013.

5. The method of claim 4 wherein said subpopulation comprises leukemic cells.

6. A method for quantifying each of a plurality of subpopulations of morphologically undistinguishable lymphocytes in a mixture thereof which method comprises contacting said mixture with a plurality of bacteria selected from the group consisting of *Arizona hinshawii*, ATTC 31241; *Escherichia coli*, NRRL-B-11009; *Escherichia coli*, NRRL-B-11010; *Escherichia coli*, NRRL-B-11011; *Bacillus globigii*, NRRL-B- 11007; *Brucella militensis*, ATCC 31242; *Corynebacterium diptheriae*,UI 43, *Corynebacterium diptheriae*, UI 44; *Corynebacterium xerosis*, NRRL-B-11008; *Sarcina luetea*, NRRL-B-11012; *Staphylococcus aureus*, ATCC 31240; *Staphylococcus aureus*, UI 57; *Staphylococcus epidermidis*, NRRL-B-11013, each of which bacteria binds to a different subpopulation or combination of subpopulations; counting the number of cells binding each of said bacteria; and calculating the concentration of each subpopulation from a predetermined pattern of selective binding between each of said bacteria and said subpopulations.

7. The method of claim 6 wherein unbound bacteria are removed and said mixture is inspected as a stained smear for the presence of bound bacteria.

8. The method of claim 6 wherein unbound bacteria are not removed and said mixture is inspected by phase contrast microscopy for the presence of bound bacteria.

9. A method for producing mutants of bacteria having a propensity for binding spontaneously to a specific subpopulation of leukocytes which comprises treating with a mutagenic agent a non-binding strain of bacteria known to require a particular nutrient for growth, bringing the treated strain into contact with said subpopulation of leukocytes to permit the association of mutants of said bacteria with said subpopulation of leukocytes, washing to remove non-binding bacteria, plating the leukocytes onto a growth medium lacking the particular nutrient required for the growth of said strain, collecting any bacteria that grow into colonies, and selecting the clones which recognize said subpopulation of leukocytes.

* * * * *

UNITED STATES PATENT OFFICE
CERTIFICATE OF CORRECTION

Patent No. 4,070,243　　　　　Dated January 24, 1978

Inventor(s) Marius C. Teodorescu et al.

It is certified that error appears in the above-identified patent and that said Letters Patent are hereby corrected as shown below:

Col. 1, line 24, "Europ M. Immunol" should be --Europ J. Immunol--

Col. 2, line 35 "delection" should be --deletion--

Col. 4, line 7, "devices" should be --devised--

Col. 5, line 38, "bond" should be --bind--

Cols. 5 & 6 (Table), heading in 3rd column, "Anti-Ig Ab" E. coli % should be --Anti-Ig Ab-- E. coli$^b$ %

Cols. 5 & 6 (Table), 4th column under heading "Ec$_2$" "58±1.9" should be --58±4.9--

Col. 9, line 55, "larges" should be --largest--

Signed and Sealed this

Thirteenth Day of June 1978

[SEAL]

Attest:

RUTH C. MASON
Attesting Officer

DONALD W. BANNER
Commissioner of Patents and Trademarks